United States Patent
Kalinowski et al.

(10) Patent No.: US 7,031,922 B1
(45) Date of Patent: Apr. 18, 2006

(54) METHODS AND DEVICES FOR ENHANCING FLUENCY IN PERSONS WHO STUTTER EMPLOYING VISUAL SPEECH GESTURES

(75) Inventors: Joseph Kalinowski, Greenville, NC (US); Andrew Stuart, Winterville, NC (US); Michael Rastatter, Greenville, NC (US)

(73) Assignee: East Carolina University, Greenville, NC (US)

( * ) Notice: Subject to any disclaimer, the term of this patent is extended or adjusted under 35 U.S.C. 154(b) by 1174 days.

(21) Appl. No.: 09/718,222

(22) Filed: Nov. 20, 2000

(51) Int. Cl.
*G10L 21/00* (2006.01)

(52) U.S. Cl. .................... 704/271; 704/275; 704/235; 434/185; 434/156; 434/178; 600/23; 600/559; 623/10

(58) Field of Classification Search ........ 704/270–278, 704/235; 434/185, 178, 156, 169; 600/23, 600/559, 372–378; 623/10; 514/546; 607/57
See application file for complete search history.

(56) References Cited

U.S. PATENT DOCUMENTS

| | | | |
|---|---|---|---|
| 3,349,179 A | 10/1967 | Klein | |
| 4,020,567 A * | 5/1977 | Webster | 434/185 |
| 4,336,524 A | 6/1982 | Levine | 340/311.1 |
| 4,464,119 A | 8/1984 | Vildgrube et al. | 434/185 |
| 4,636,866 A | 1/1987 | Hattori | 358/236 |
| 4,695,129 A | 9/1987 | Faessen et al. | 350/96.25 |
| 4,856,045 A | 8/1989 | Hoshina | 379/53 |
| 4,916,441 A | 4/1990 | Gombrich | 340/712 |
| 4,934,773 A | 6/1990 | Becker | 350/6.6 |
| 5,003,300 A | 3/1991 | Wells | 340/705 |
| 5,048,077 A | 9/1991 | Wells et al. | 379/96 |
| 5,106,179 A | 4/1992 | Kamaya et al. | 351/158 |
| 5,111,498 A | 5/1992 | Guichard et al. | 379/53 |
| 5,138,312 A | 8/1992 | Tsukakmoto et al. | 340/825.44 |
| 5,189,632 A | 2/1993 | Paajanen et al. | 364/705.05 |
| 5,281,957 A | 1/1994 | Schoolman | 345/8 |
| 5,347,400 A | 9/1994 | Hunter | 359/815 |
| 5,485,318 A | 1/1996 | Lebby et al. | 359/811 |
| 5,485,504 A * | 1/1996 | Ohnsorge | 455/566 |

(Continued)

OTHER PUBLICATIONS

"Excuse me, is that a monitor on your head?", CNN.com, http://www.cnn.com/2000/TECH/computing/03/31/head-monitor.idg/index.html (Aug. 30, 2000).

(Continued)

*Primary Examiner*—Vijay B. Chawan
(74) *Attorney, Agent, or Firm*—Myers Bigel Sibley & Sajovec PA

(57) ABSTRACT

Methods, devices, and computer program products display visual choral speech to a patient who stutters or has a speech impediment or impairment as a visual stimulus for the patient to enhance the fluency of the patient. The visual choral speech is incongruous with the speech produced by the stutterer and is provided by a visual display of the articulatory movements of a person other than the patient (or a simulated representation thereof) of the person's lips and mouth as the person speaks. The visual speech gestures can be displayed to the patient in advance of a speaking event or speech production by the stutterer and/or concurrently with a speaking event (either intermittently or continuous during the speaking event). The visual choral speech gestures can be based on a string of coherent words to provide the visual speech gestures signal such that it is relayed to the user without the attendant auditory component allowing the user to speak at a substantially normal pace with enhanced fluency.

70 Claims, 8 Drawing Sheets

U.S. PATENT DOCUMENTS

| | | | | |
|---|---|---|---|---|
| 5,561,538 | A | 10/1996 | Kato et al. | 359/40 |
| 5,596,451 | A | 1/1997 | Handschy et al. | 359/633 |
| 5,647,834 | A | 7/1997 | Ron | 600/23 |
| 5,741,136 | A * | 4/1998 | Kirksey et al. | 434/169 |
| 5,765,135 | A * | 6/1998 | Friedman et al. | 704/276 |
| 5,790,798 | A * | 8/1998 | Beckett et al. | 709/224 |
| 5,794,203 | A * | 8/1998 | Kehoe | 704/271 |
| 5,826,427 | A | 10/1998 | Faris | 349/5 |
| 5,938,447 | A * | 8/1999 | Kirksey | 434/169 |
| 5,961,443 | A | 10/1999 | Rastatter et al. | 600/23 |
| 5,982,853 | A * | 11/1999 | Liebermann | 379/52 |
| 6,073,034 | A | 6/2000 | Jacobsen et al. | 455/566 |
| 6,231,500 | B1 * | 5/2001 | Kehoe | 600/23 |
| 6,505,208 | B1 * | 1/2003 | Kanevsky et al. | 707/102 |
| 6,754,632 | B1 * | 6/2004 | Kalinowski et al. | 704/271 |

OTHER PUBLICATIONS

"New Wired Clothing Comes with Personal Network," cnn.com/2000/TECH/computing/08/18/wired.jacket.idg/index.html (posted on Aug. 18, 2000).

"Visions of wearable Internet ware," CNN.com, http://www.cnn.com/2000/STYLE/fashion06/26/wearable.computers/index.html (Aug. 30, 2000).

Adams et al., "The Effects of Auditory Masking on the Anxiety Level, Frequency of Dysfluency, and Selected Vocal Characteristics of Stutterers," J. Speech Hear. Res., 15, pp. 572-578 (1972).

Andrews et al. "Stuttering: A Review of Research Findings and Theories," circa 1982, J. Speech Hear. Disord., 48, pp. 226-246 (Aug. 1983).

Andrews et al., "Stuttering: Speech Pattern Characteristics Under Fluency-Inducing Conditions," J. Speech Hear. Res., 25, pp. 208-215 (Jun. 1982).

Bakker, K. "Clinical Technologies for the Reduction of Stuttering and Enhancement of Speech Fluency," Seminars in Speech and Language, 20 (3), pp. 271-279 (1999).

Barber, V. "Studies in the Psychology of Stuttering: XV. Chorus Reading as a Distraction in Stuttering," J. Speech Disord., 4, pp. 371-383 (1939).

Calvert et al., "Activation of Auditory Cortex During Silent Lipreading," Science, vol. 276, pp. 593-596 (Apr. 25, 1997) http://www.scienemag.org.

Cherry et al., "Experiments Upon Total Inhibition of Stammering by External Control and Some Clinical Results," J. Psychosom. Res., 1, pp. 233-246 (1956).

Conture, E.G., "Some Effects of Noise on the Speaking Behavior of Stutterers," J. Speech Hear. Res., 17, pp. 714-723 (1974).

Dodd, "Interaction of auditory and visual information in speech perception," British Journal of Psychology, vol. 71, pp. 541-549 (1980).

Erber, "Auditory-Visual Perception of Speech," Journal of Speech and Hearing Disorders, pp. 481-492 (1975).

Fox et al., "A PET Study of the Neural Systems of Stuttering," Nature, 382, pp. 158-161 (Jul. 11, 1996).

Hargrave et al., "Effect of Frequency-Altered Feedback on Stuttering Frequency at Normal and Fast Speech Rates," J. of Speech and Hearing Res., 37, pp. 1313-1319 (Dec. 1994).

Howell et al., "Automatic Recognition of Repetitions and Prolongations in Stuttered Speech," C. W. Starkweather and H.F.M. Peters (Eds.), Proceedings of the First World Congress on Fluency Disorders, vol. II, pp. 372-374), The Netherlands University Press, Nijmegen (1995).

Howell et al., "Automatic Stuttering Frequency Counts," W. Hulstijn, et al. (Eds.), Speech Production: Motor Control, Brain Research and Fluency Disorders, Amsterdam, Elsevier Science, pp. 395-404 (1997).

Howell et al., "Development of a Two-Stage Procedure for the Automatic Recognition of Dysfluencies in the Speech of Children Who Stutter: I. Psychometric Procedures Appropriate for Selection of Training Material for Lexical Dysfluency Classifiers," Journal of Speech, Language, and Hearing Research, vol. 40, pp. 1073-1084 (Oct. 1997).

Howell et al., "Development of a Two-Stage Procedure for the Automatic Recognition of Dysfluencies in the Speech of Children Who Stutter: II. ANN Recognition of Repetitions and Prolongations with Supplied Word Segment Markers," Journal of Speech, Language, and Hearing Research, vol. 40, pp. 1085-1096 (Oct. 1997).

Jayant, Nikil et al., "Signal Compression Based on Models of Human Perception," Proceedings of the IEEE, vol. 81, No. 10, pp. 13851422 (1993).

Johnson et al., "Studies in the Psychology of Stuttering: VII. Effect of Certain Changes in Speech Pattern Upon Frequency of Stuttering," J. Speech Disord., 2, pp. 105-109 (1937).

Kalinowski et al., "Effect of Normal and Fast Articulatory Rates on Stuttering Frequency," J. of Fluency Disorders, 20, pp. 293-302 (1995).

Kalinowski et al., "Effects of Alterations in Auditory Feedback and Speech Rate on Stuttering Frequency," Language and Speech, 36 (1), pp. 1-16 (1993).

Kalinowski et al., "Inducement of Fluent Speech in Persons Who Stutter Via Visual Choral Speech," Neurosci. Lett., 280, pp. 1-3 (2000).

Kalinowski et al., "Stuttering Amelioration at Various Auditory Feedback Delays and Speech Rates," European Journal of Disorders of Communication, 31, pp. 259-269 (1996).

Kuniszyk-Jozkowiak et al., "Effect of Acoustical, Visual, and Tactile Reverberation on Speech Fluency of Stutterers," Folia Phoniatr. Lopgop., 49, pp. 26-34 (1997).

Kuniszyk-Jozkowiak et al., "Effect of Acoustical, Visual, and Tactile Echo on Speech Fluency of Stutterers," Folia Phoniatr. Lopgop., 48, pp. 193-200 (1996).

MacLeod et al., "Effect of Single and Combined Altered Auditory Feedback on Stuttering Frequency At Two Speech Rates," J. of Commun. Disorders, 28, pp. 217-228 (1995).

Massaro et al., "Evaluation and Integration of Visual and Auditory Information in Speech Perception," Journal of Experimental Psychology, Human Perception and Performance, vol. 9, No. 5, pp. 753-771 (1983).

Massaro et al., "Perception of asynchronous and conflicting visual and auditory speech," J. Acoust. Soc. Am. vol. 100, No. 3, pp. 17771786 (Sep. 1996).

May et al., "Some Effects of Masking and Eliminating Low Frequency Feedback on the Speech of Stammerers," Behav. Res. & Therapy, 6, pp. 219-223 (1968).

McGurk et al., "Hearing lips and seeing voices," Reprinted from Nature, vol. 264, pp. 746-748 (1976).

Perkins, "From Pscyhoanalysis to Discoordination," H.H. Gregory (Ed.) "Controversies About Stuttering Therapy," pp. 97-127, University Press (1979).

Perkins et al., "Phone Rate and the Effective Planning Time Hypothesis of Stuttering," 29. J. of Speech and Hearing Res., 22, pp. 747-755 (Dec. 1979).

Puce et al., "Differential Sensitivity of Human Visual Cortex to Faces, Letterstrings, and Textures: A Functional Magnetic Resonance Imaging Study," J. Neurosci, vol. 16, No. 16, pp. 5205-5215 (Aug. 15, 1996).

Sams et al., "Face-Specific Response from the Human Inferior Occipito-Temporal Cortex," Neurosci., vol. 77, No. 1, pp. 49-55 (1997).

Sams et al., "Seeing speech: visual information from lip movements modifies activity in the human auditory cortex," Neuroscience Letters, vol. 127, pp. 141-145 (1991).

Stuart et al., "Fluent Speech, Fast Articulatory Rate, and Delayed Auditory Feedback: Creating a Crisis for a Scientific Revolution?" Perceptual and Motor Skills, 82, pp. 211-218 (1996).

Tye-Murray, "Visual feedback during speech production," J. Acoust. Soc. Am., vol., 79, No. 4, pp. 1169-1171 (Apr. 1986).

Wu et al., "A Position Emission Tomograph [18F] Deoxyglucose Study of Developmental Stuttering," Neuroreport, 6, pp. 501-505 (1995).

Adams, Martin, "Comment on 'Interpreting Results of the Fluent Speech Paradigm in Stuttering Research: Difficulties in Separating Cause From Effect,'" Letters to the Editor, J. Speech Hear. Res., 37, pp. 813-815 (1994).

Armson et al., "A Model of Stuttering Remediation: Multiple Factors Underlying Fluency Enhancement," In C.W. Starkweather and H.F.M. Peters (Eds.), Stuttering: Proceedings from The First World Congress on Fluency Disorders, University Press, Nijmegen, The Netherlands, pp. 296-300 (1995).

Kalinowski et al. (2003). *Choral Speech: The Amelioration of Stuttering via Imitation and the Mirror Neuronal System.* Neuroscience and Behavioral Reviews 27, pp. 339-347.

Kalinowski et al. (2003). *Speaking with a mirror: engagement of mirror neurons via choral speech and its derivatives induces stuttering inhibition,* Medical Hypotheses, 60, pp. 538-543.

* cited by examiner

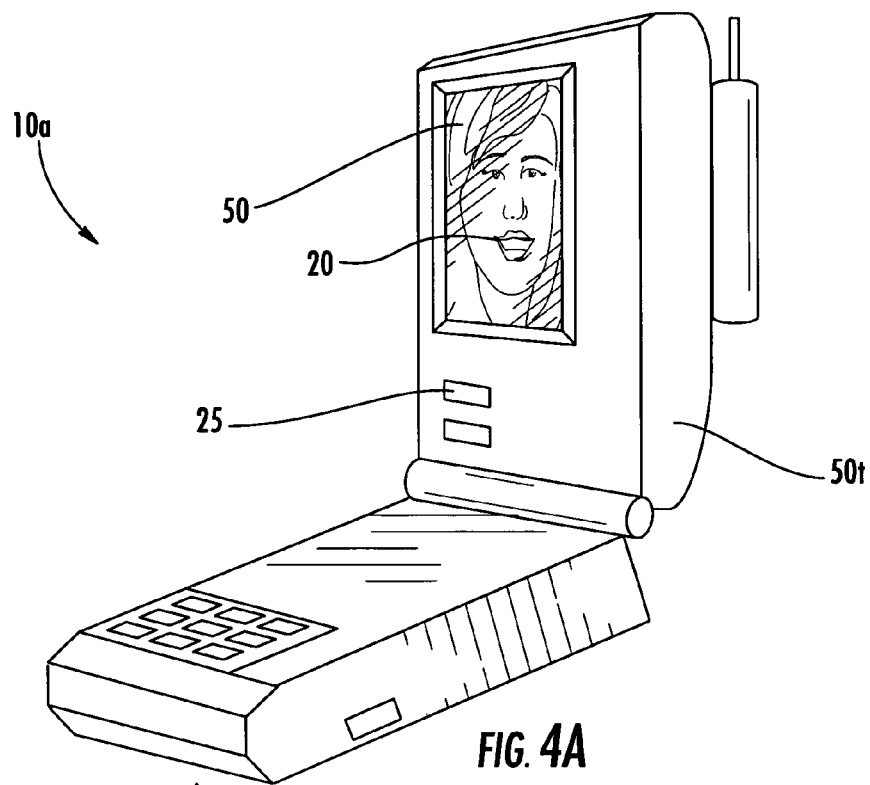
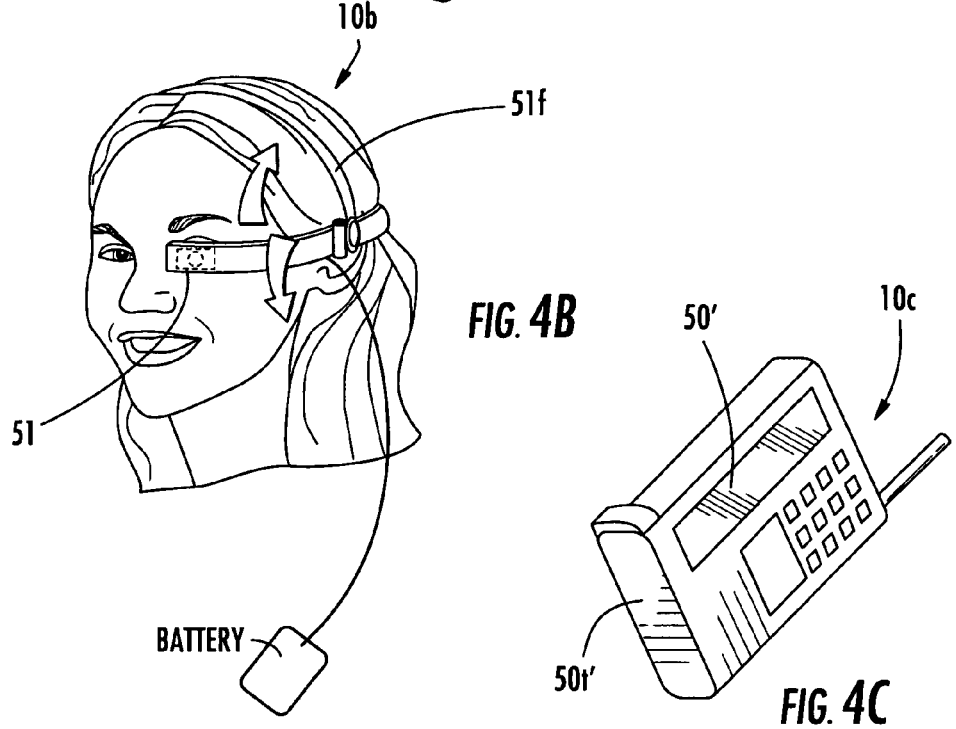
FIG. 4A
FIG. 4B
FIG. 4C

METHODS AND DEVICES FOR ENHANCING FLUENCY IN PERSONS WHO STUTTER EMPLOYING VISUAL SPEECH GESTURES

FIELD OF THE INVENTION

The present invention relates to devices and methods for enhancing the fluency of persons who stutter.

BACKGROUND OF THE INVENTION

Conventionally, stuttering has been treated by several different types of treatment, including psychiatric therapy, drug therapy, and the use of altered auditory feedback, generated by electrical signal processing devices, relayed to the person who stutters. These techniques can be generally characterized as either endogenous alterations of the speech signal output or "motoric strategies", such as prolonged or slowed speech, rhythmic speech, singing, and lipped speech, or exogenous dynamic alterations of the speech signal itself ("altered auditory feedback strategies"), both of which can successfully induce relatively fluent speech in people who stutter. See, e.g., O. Bloodstein, *A Handbook on Stuttering* (5$^{th}$ ed. Singular, San Diego, Calif., 1995). Unfortunately, the ameliorative effects of these phenomena are generally temporary and are thought to need to be engaged in relatively constantly to reduce stuttering frequency. See Kalinowski et al., *Inducement of fluent speech in persons who stutter via visual choral speech,* 280 Neuroscience Letters, pp. 1–3(Elsevier Science Ireland Ltd, 2000).

Two types of altered auditory feedback which have been used to treat stuttering include delayed auditory feedback ("DAF") and the introduction of a masking noise or masked auditory feedback ("MAF"). Generally described, DAF imposes a delay on the delivery of a feedback speech signal to a speaker/stutterer, while MAF serves to compete with a speaker's auditory feedback.

For example, M. E. Wingate, in *Stuttering: theory and treatment*, p. 237 (Irvington, 1976), describes a type of altered auditory feedback which can include DAF to provide emphasis on phonation, i.e., slowing speech down to extend syllable duration. However, this type of auditory feedback or fluency enhancement is conventionally thought to be achievable with or without the use of DAF as long as syllable prolongation was employed. See, e.g., W. H. Perkins, *From Psychoanalysis to Discoordination*, in H. H. Gregory (Ed.) *Controversies about stuttering therapy*, pp. 97–127 (University Press, 1979). See also Andrew Stuart et al., *Fluent Speech, Fast Articulatory Rate, and Delayed Auditory Feedback: Creating a Crisis for A Scientific Revolution?*, 82 Perceptual and Motor Skills, pp. 211–218 (1996).

Generally stated, the reduction in stuttering frequency under speech signal alterations has been attributed to entrained rhythm, distraction, modified vocalization, and rate reduction. Indeed, in the past, slowed speech rates were found to be an important factor in the reduction of stuttering. For example, in W. H. Perkins et al., *Phone rate and the effective planning time hypothesis of stuttering,* 29 Jnl. of Speech and Hearing Research, 747–755 (1979), the authors reported that stuttering was virtually eliminated when speakers reduced speech rate by approximately 75%. However, other reports have found that rate reduction is neither necessary, nor sufficient, for fluency enhancement. See Kalinowski, et al., *Stuttering amelioration at various auditory feedback delays and speech rates,* European Journal of Disorders of Communication, 31, 259–269 (1996); Stuart et al., *Fluent speech, fast articulatory rate, and delayed auditory feedback: Creating a crisis for a scientific revolution?,* Perceptual and Motor Skills, 82, 211–218 (1996); MacLeod, et al., *Effect of single and combined altered auditory feedback on stuttering frequency at two speech rates,* Journal of Communication Disorders, 28, 217–228 (1995); Kalinowski et al., *Effect of normal and fast articulatory rates on stuttering frequency,* Journal of Fluency Disorders, 20, 293–302 (1995); Hargrave et al, Effect of frequency-altered feedback on stuttering frequency at normal and fast speech rates. Journal of Speech and Hearing Research, 37, 1313–1319 (1994); and Kalinowski et al., Effects of alterations in auditory feedback and auditory feedback and speech rate on stuttering frequency. Language and Speech, 36, 1–16 (1993).

Recently, a portable therapeutic device and related stuttering enhancement treatment methods were described in U.S. Pat. No. 5,961,443 to Rastatter et al., the contents of which are hereby incorporated by reference as if recited in full herein. These devices and methods employ altered auditory feedback (auditory delay and/or frequency shift signals) to be delivered to a stutterer via a portably configured device.

SUMMARY OF THE INVENTION

Embodiments of the present invention provides methods and devices which employ the use of visual choral speech (meaning "visual speech gestures") as a fluency enhancing stimulus visually relayed to the patient (the person with a tendency to stutter) during and/or in advance of speech output by the patient. The visual choral speech can be coherent or incoherent and can be incongruent with the speech content output by the patient. The visual choral speech stimulus of the present invention is used as a visual aid or stimulus for a patient which can allow the patient to speak at a substantially normal pace with enhanced fluency and may not require the use of altered auditory feedback strategies. The visual choral speech stimulus of the present invention can be used with forms of auditory feedback or other forms of treatments as well.

In particular embodiments of the present invention, the visual stimulus provided by the visual choral speech or visual speech gestures of the instant invention are representative of the articulatory movements of a person's face as the person generates spoken speech. That is, the visual choral speech stimulus of the instant invention preferably may employ visual (dynamic or moving) images of the articulatory movement of at least the lips and mouth of a person (either from the patient or from an individual or individuals other than the patient) corresponding to the movements of the lips and mouth made as a person speaks. The visual choral speech or visual speech gestures of the instant invention may also include surrounding anatomical regions such as the jaw, face, and the upper torso or the entire body.

In further embodiments of the present invention, the visual choral speech stimulus may be delivered to the patient such that any attendant auditory component is inaudible to the patient. The visual choral speech stimulus may be silent such that it is displayed and relayed to the patient without any attendant sound. Thus, the visual choral speech may be relayed or displayed to the patient in a minimally or non-disruptive manner even to persons in proximity to the patient using certain embodiments of the devices and methods of the present invention. This quiet stimulus can be an unobtrusive stuttering aid. The visual presentation of the visual stimulus can be selectively activated by the patient to be operative in conjunction with a speaking event by the patient.

In still additional embodiments of the present invention, methods for enhancing the fluency of persons who stutter include: (a) displaying visual speech gestures associated with the articulatory movements of a person's mouth on a display while the patient who has a stuttering or speech impediment is speaking so that the patient is able to visually perceive the articulatory movements of the person's mouth provided on the display such that the patient is able to refer to the display at desired times. Such methods may thereby enhance the fluency of the speech of the patient.

In other embodiments of the present invention, devices are provided which include a display device, and a display controller operably associated with the display device. The device is configured to cause the display controller to visually present on the display device at least one predetermined visual speech gesture stimulus associated with the articulatory movements of a person speaking coherent text which is incongruous with the speech production of a user.

In further embodiments, the visual speech gestures are output from the device without any attendant auditory signal (or so that any auditory signal is suppressed or inaudible to the user/patient). The display can be configured to allow the patient to adjust the field of view or presentation of the visual display (such as to zoom (in or out) to the facial or mouth region as desired).

The visual presentation on the display can enlarge or focus on the mouth of a person to make the mouth (and/or face and mouth) the prominent feature in the visual display. That is, the display can present the person such that the articulatory movements are easily viewable without other environmental or visual distractions in the image display. The display can present the visual stimulus images so as to make the lips, the lips and mouth, and/or the lips, mouth and face the prominent in the image and thus to enhance the ease of viewability of the articulatory movements in the displayed stimulus image.

In additional embodiments, the methods and devices of the present invention can additionally output an auditory stimulus which is unrelated to the visual stimulus (the visual speech gestures noted above). The auditory stimulus can be auditory natural spoken speech signals such as sustained vowel sounds and the like.

The visual speech gesture signal(s) can be displayed from miniaturized display screens or "micro-displays" such as active matrix LCD's incorporated into head mounted displays or handheld devices such as pagers, mobile or wireless telephones, or (wrist) watches, bracelets, or other proximately worn (within the visual range of the user) items such as glasses, hats, and the like. The head mounted display can be visually relayed to a single eye or both eyes of the patient. The display screens can also be monitors associated with general-purpose computers, laptop computers, or teleprompters and the like.

As noted above, devices according to embodiments of the present invention can be configured to provide both a visual speech gesture stimulus and an auditory speech gesture stimulus signal which is preferably incongruent with the visual speech gesture stimulus. For example, the visual speech gestures can correspond to famous lyrics, nursery rhymes, the pledge of allegiance, and the like, while the auditory stimulus is an independent and incongruent exogenously generated auditory spoken speech stimulus signal in the form of an entrained vowel or consonant. The latter is described in co-pending and co-assigned U.S. patent application entitled, *Methods and Devices for Delivering Exogenously Generated Speech Signals to Enhance Fluency in Persons Who Stutter*, identified by Attorney Docket No. 5218-83. The disclosure of which is hereby incorporated by reference as if recited in full herein.

While embodiments of the present invention have been described above primarily with reference to methods and devices, as will be appreciated by those of skill in the art, the present invention may be provided as methods, systems, or devices and computer program products.

BRIEF DESCRIPTION OF THE DRAWINGS

FIGS. 4A–4E illustrate exemplary devices which can transmit or display visual speech gestures to the user according to embodiments of the present invention.

DESCRIPTION OF PREFERRED EMBODIMENTS

Figure 1:
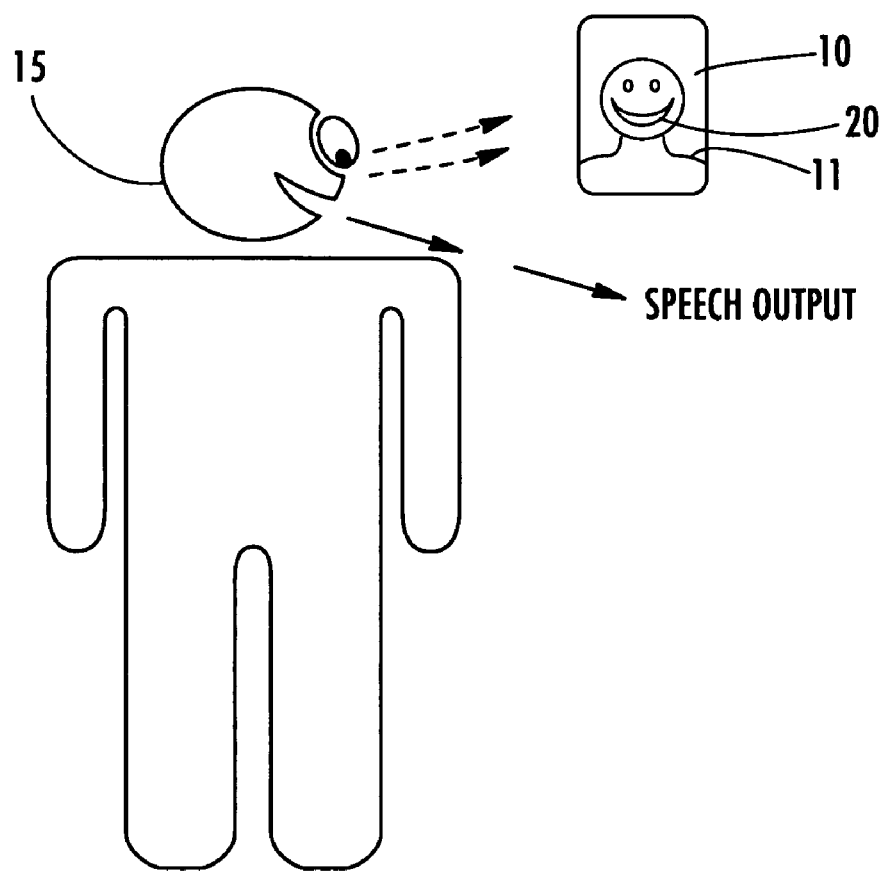
FIG. 1 is a schematic illustration of a device configured to visually relay visual speech gestures as a fluency-enhancing stimulus to a user according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, layers, regions, or components may be exaggerated for clarity.

As described in more detail below, embodiments of the invention employ the use of visual choral speech (meaning "visual speech gestures") as a fluency-enhancing stimulus visually relayed to the patient (the person with a tendency to stutter) during and/or in advance of, speech output by the patient. The visual choral speech can be coherent or incoherent and can be incongruent with the speech content output by the patient. The visual choral speech stimulus may be used to allow a patient to speak at a substantially normal pace with enhanced fluency without requiring the use of altered auditory feedback strategies. The visual choral speech stimulus can be used with forms of auditory feedback or other forms of treatments (such as to improve fluency when combined or coupled with traditional therapeutic motoric strategies) some examples of which will be discussed further below.

The visual choral speech or visual speech gestures may be representative of the articulatory movements of a person's face as the person generates spoken speech. That is, the visual choral speech stimulus of the instant invention can employ visual (dynamic or moving) images of the articulatory movement of at least the lips and mouth of a person (preferably from an individual or individuals other than the patient) corresponding to the lip and mouth movements made as the person speaks. The visual stimulus which provides the visual choral speech or visual speech gestures of the instant invention may also include other portions of the anatomy in the visual displays, such as the jaw, the entire face, the head, the upper torso, or the entire body.

The visual choral speech may be delivered to the patient such that the attendant auditory component (if any) is inaudible to the patient. The visual choral speech stimulus may be silent such that it is displayed and relayed to the patient without any attendant sound. Thus, the visual choral speech may be relayed or displayed to the patient in a minimally or non-disruptive manner even to persons in proximity to the patient using the devices and visual stimulus of the present invention. Indeed, other persons adjacent the patient during speech may not even be aware of that the patient is using a fluency-enhancing visual choral stimulus. Thus, the visual speech gestures may be generated by having a person "silently" read or "lip" the desired speech or the output of the display signal can be configured to suppress any attendant auditory signal from normally spoken speech.

The visual speech gestures in particular embodiments of the present invention may correspond to coherent speech. That is, the visual speech gestures may be generated by the formation of a string of actual words of meaningful written text or meaningful oral communication (such as the recitation of words in a sentence, or a paragraph or text or passages in a story, song or poem). The visual speech gestures may also correspond to single words recited serially (such as "apple" "banana" "car" "dinosaur" and the like). The visual speech gestures may also correspond to incoherent speech, which, when spoken, has no recognizable definable meaning. For example, rhyming syllables, such as "pat-tat", "rat-tat-tat", "dum-dee-dum", "putt-tutt", "tat-a-tat", or other non-word utterances such as "blah-blah", "da-da", and the like. The visual choral speech gestures may be generated at a substantially normal speaking pace.

In other embodiments, the visual speech gestures correspond to speech which is incongruent with the speech output of the patient but corresponds to strings of words which are coherent and recognizable to the patient. For example, recognizable coherent speech includes famous or well-known lyrics, nursery rhymes, famous speeches, poems, the alphabet, counting (reciting the numbers in a predictable pattern such as "1-2-3" or "10-20-30") or other well known text such as the Pledge of Allegiance, the Star Spangled Banner, (and similar well known text or lyrics or poems for persons of other languages or located in other national countries) and the like. While not being limited to any particular theory of operation, it is anticipated that the closer the visual speech gestures are to recognizable speech, the greater efficacy and/or reliability of the visual stimulus to induce fluency by triggering the auditory cortex of the speaker/patient.

In yet other embodiments, the content or meaning of the visual speech gestures is incongruent with the speech output of the patient but generally corresponds to the topic of the speech of the patient. For example, for a patient planning on speaking on a particular topic (such as a public speech on the results of a new pharmaceutical drug) the visual speech gestures can be made by a person reading text on clinical applications or advancements in the treatment of a disease using pharmaceutical drugs.

Figure 3:
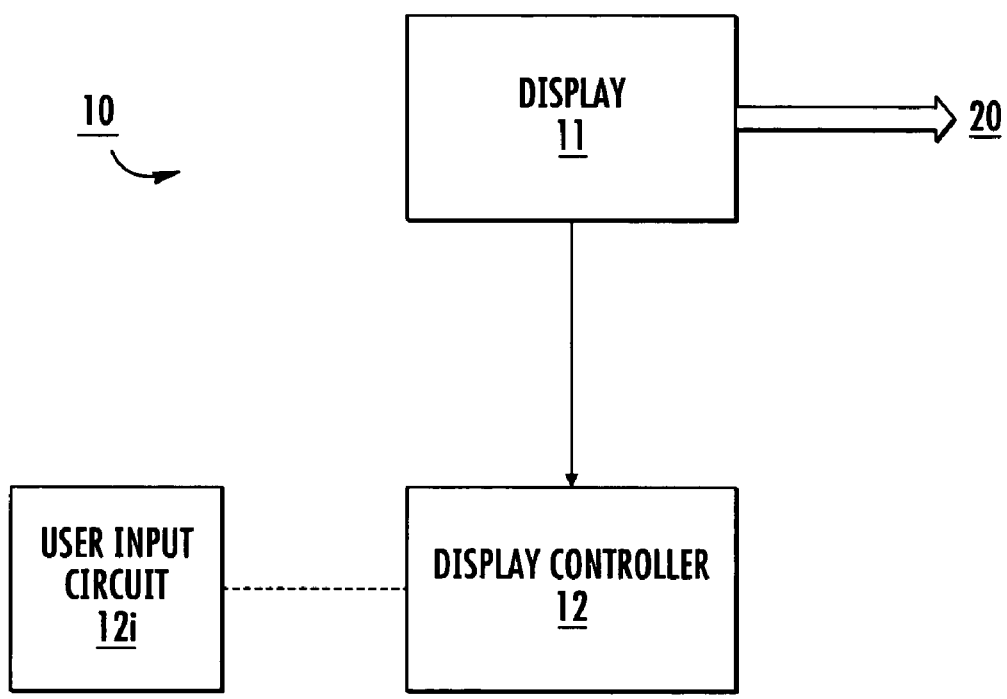
FIG. 3 is a schematic illustration of a device according to embodiments of the present invention.

As shown in FIG. 1, the systems of the present invention may include a display device 10 which, in operation can be positioned to be in visual communication with the patient 15 while the patient is speaking. For example, as shown in FIG. 1, the device 10 may be configured as a handheld portable device which can be easily positioned in a desired visually appropriate position according to the needs of the patient/user. For example, such a portable handheld device can be positioned on a desk or a podium such that the display 11 showing the visual speech gestures 20 can be easily visually referenced by the user at the desired times while speaking. FIG. 3 schematically illustrates one embodiment of the device 10 which includes a display 11 operably associated with a display controller 12. The display controller 12 may be a dedicated device, or a general purpose processing system, and/or a combination of dedicated devices or general-purpose devices or systems. The display controller 12 may also be embodied as hardware, software or a combination of hardware and software.

The display controller 12 can be configured to repeatedly output the visual speech gesture stimulus 20 to a user/patient at desired times such as at times corresponding to an episodic stuttering event on the part of the user, in advance of the production of speech by the user, and during the production of speech by the user. As shown in FIG. 3, the device 10 can also include a standby mode and an active display mode. A user input circuit 12i can be operably associated with the display device 10 to cause the display device to enter the active display mode and display the visual speech gestures 20 substantially immediate of a user activating the user input circuit 12i. (The user input circuit 12i can also be configured to activate an auditory stimulus 40 which is unrelated to the visual stimulus as will be discussed further below).

The visual speech gestures can be configured so that the articulatory movements are the prominent features in the display (for example, by excluding background or peripheral images, or to display substantially only the face or mouth of the person, or to fill the display area with the desired anatomical regions sufficient to make the visual speech gestures prominent and readily discernable by the user at desired times during speech on the part of the user).

Figure 2:
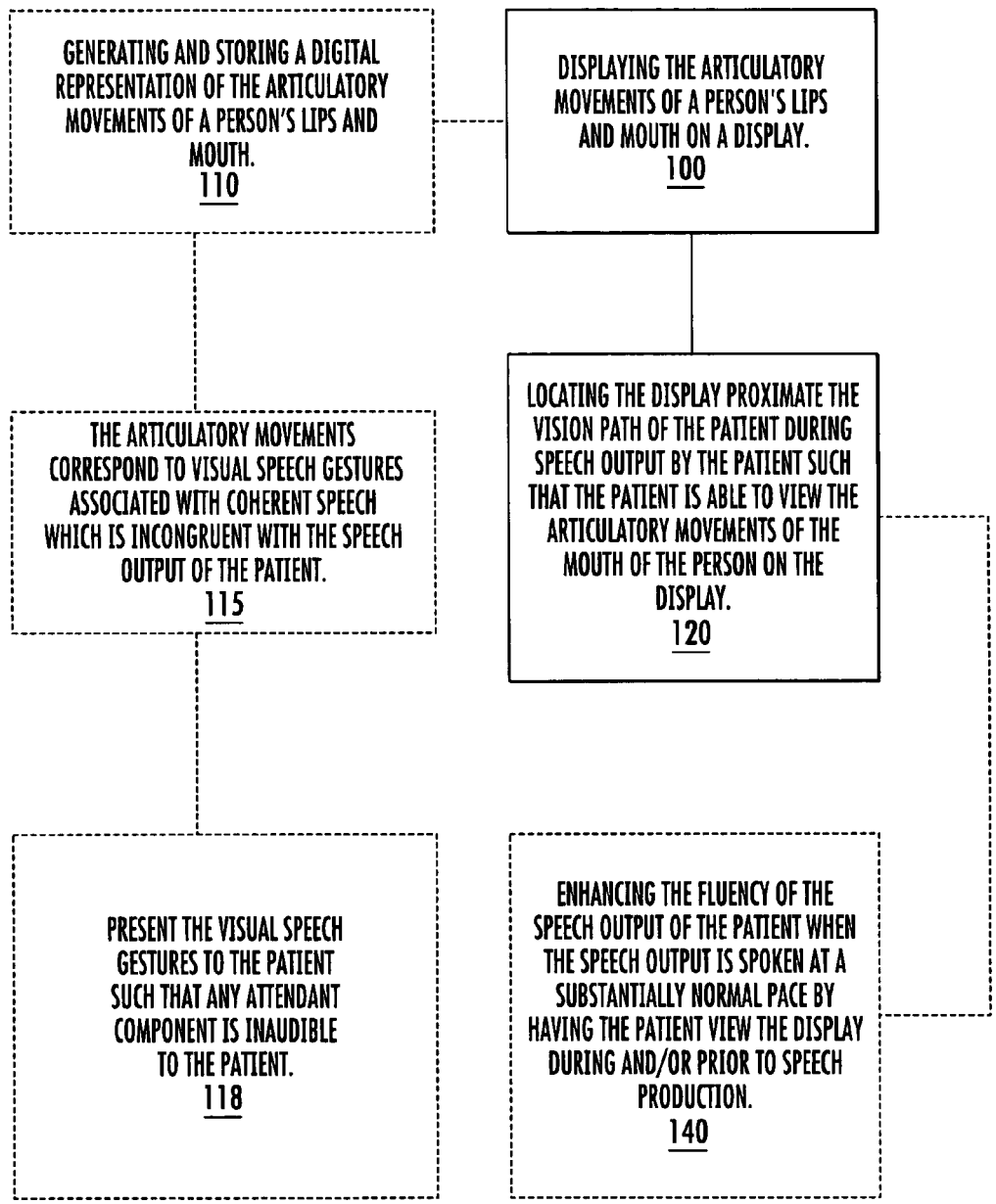
FIG. 2 is a block diagram of operations for enhancing the fluency of a person who stutters according to embodiments the present invention.

FIG. 2 illustrates operations for increasing the fluency of the stutterer by displaying the exogenously generated articulatory movements of the person's lips and mouth on a display (Block 100). The display is located proximate the vision path of the patient during speech output or production on the part of the patient such that the patient is able to view the articulatory movements of the lips or mouth of the person on the display (Block 120). In certain embodiments the fluency of the speech output of the patient can be enhanced when the speech output of the patient is spoken at a substantially normal pace by having the patient view the display during and/or prior to speech production (Block 140). (It is noted that "optional" features or steps are generally represented by dotted lines in the figures.) In particular embodiments, the articulatory movements of a person's lips and mouth are generated and stored so that the image can be digitally represented and displayed to the patient at the desired times (Block 110). Optionally, the articulatory movements correspond to visual speech gestures associated with coherent speech which is incongruent with the speech output or production of the patient (Block 115). It is preferred that the visual speech gestures are presented to the patient such that any attendant auditory output associated with the visual speech gestures is inaudible to the patient (Block 118).

The present invention can also be carried out by computer program products that when implemented on appropriate devices can enhance the fluency of persons who stutter. The computer program product can comprise computer readable program code for displaying at least one visual speech gesture stimulus associated with the articulatory movements of a person's mouth on a display while a patient having a stuttering or speech impediment is speaking so that the patient is able to visually perceive the articulatory movements of the person's mouth provided on the display such that the patient is able to refer to the display at desired times so that the at least one visual speech gesture stimulus is provided by a person other than the patient.

The visual speech gestures stimulus of the instant invention can be displayed from displays associated with general purpose computers, laptop computers, embedded systems, and/or personal digital assistants (PDAs), smartphones, teleprompters or miniaturized display screens or systems or "micro-displays" such as active matrix LCD's incorporated into head mounted displays or handheld devices such as, or miniaturized, handheld, palm, or wearable computers, pagers, mobile or wireless telephones, or (wrist) watches, bracelets, or other proximately worn (within the visual range of the user) items such as glasses, hats, and the like. The head mounted display can be visually relayed to a single eye or both eyes of the patient. Examples of devices which may be utilized in embodiments of the invention are illustrated in FIGS. 4A–4E. However, the present invention should not be construed as limited to such examples but may be utilized with any device capable of displaying visual speech gestures according to embodiments of the present invention.

As shown in FIG. 4A, the device 10a is configured such that the display 11 and display controller 12 are incorporated into a telephone 50t having display 50 such that it is incorporated into a telephone 50t. The display 50 can also be used as a videophone with a built in image processor to display the auditory stimulus on a portion of the display 50 or to override the incoming video display as needed. As discussed above, and shown for illustrative purposes in FIG. 4A, the device 10a can include a "zoom" 25 to allow a user to zoom in and out to adjust the focal length to adjust the presented image about the mouth region in the display 50 according to the needs or desires of the patient. See U.S. Pat. Nos. 5,111,498 and 4,856,045 for descriptions of display terminals suitable for a videophone, the contents of which are hereby incorporated by reference as if recited in full herein. Of course, the display 11 can be provided as a separate component such as proposed in U.S. Pat. No. 4,934,773 to Becker, entitled *Miniature Video Display System*, or U.S. Pat. No. 5,596,451 to Handschy et al., entitled *Miniature Image Generator Including Optics Arrangement*. The disclosures of which are hereby incorporated by reference as if recited in fill herein.

In embodiments illustrated in FIG. 4B, the device 10b includes as the display 11, a head mounted display 51 such that the visual speech gesture images are displayed directly into or proximate to at least one of the user's eyes, providing a virtual image without blocking the user's vision. See *Excuse me, is that a monitor on your head?*, CNN.com/2000/TECH/computing/03/31/head.monitor.idg/index.html. See also, U.S. Pat. No. 5,003,300 to Wells, entitled *Head Mounted Display For Miniature Video Display System*; U.S. Pat. No. 4,695,129 to Faessen et al., entitled *Viewer having Head Mounted Display for Cinerama Pictures*; and U.S. Pat. No. 4,636,866 to Hattori, entitled *Personal Liquid Crystal Image Display*, the disclosures of which are hereby incorporated by reference as if recited in full herein.

As shown in FIG. 4C, the display 11 may be is built into a wireless communication device 50t' as a display 50'. See e.g., U.S. Pat. No. 5,189,632 to Paajanen et al., entitled, *Portable Computer and Mobile Telephone Device*; U.S. Pat. No. 6,073,034 to Jacobsen et al., entitled *Wireless Telephone Display System*, and U.S. Pat. No. 5,485,504, to Ohnsorge, entitled *Hand-Held Radiotelephone with Video Transmission and Display*, the disclosures of which are hereby incorporated by reference as if recited in full herein. See also U.S. Pat. No. 5,138,312 to Tsukamoto et al., entitled *Pager With A Television Function*, describing displaying a TV image on a pager; and U.S. Pat. No. 4,336,524 to Levine, entitled *Video Display Pager Receiver With Memory*, the disclosures of which are hereby incorporated by reference as if recited in full herein.

Figure 4D:
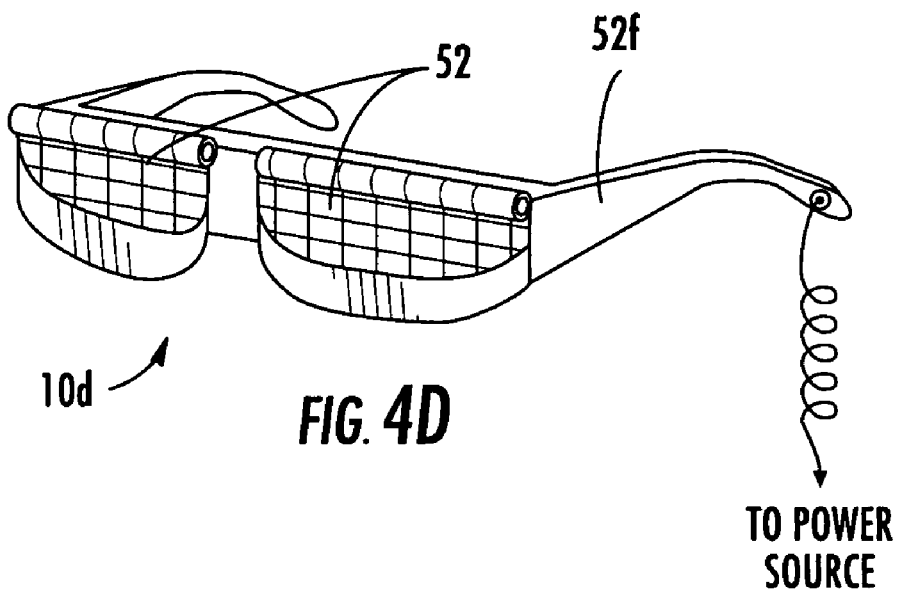

As shown in FIG. 4D, in the device 10d the display 11 may be built into eyeglass frames 52f as display 52 where the display 52 covers a portion of the vision path and/or can be rotated as desired by the user to be moveably placed out of the vision path when not in use. See U.S. Pat. No. 5,281,957 to Schoolman, entitled *Portable Computer and Head Mounted Display*, the disclosure of which is hereby incorporated by reference as if recited in full herein. See also U.S. Pat. No. 5,106,179 to Kamaya entitled *Eyesight Auxiliary Liquid Crystal Device*, describing head mounted band like frame and display and methods for projecting images directly onto the retina of the user's eyes, the disclosure of which is hereby incorporated by reference as if recited in full herein.

Figure 4E:
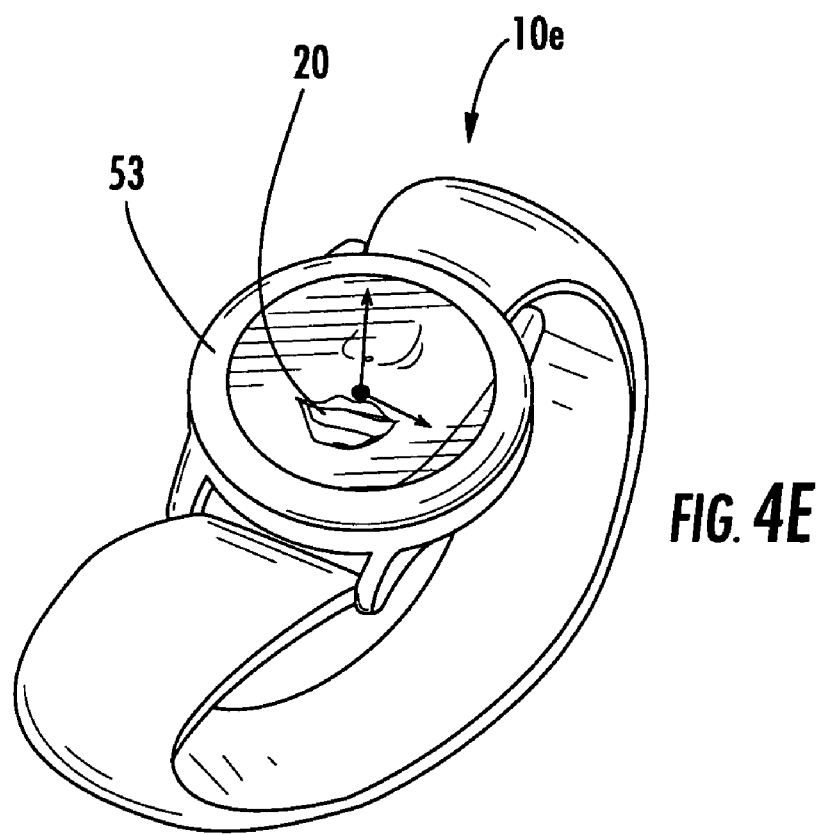

FIG. 4E illustrates another exemplary wearable device 10e. In this embodiment, the display 11 is presented on the face of a wristwatch 10e as display 53. The wristwatch can include analog arms overlying the display 53 or a digital representation of same which can be suppressed to enhance the visual speech gestures stimulus 20 on the display 53.

Figure 5:
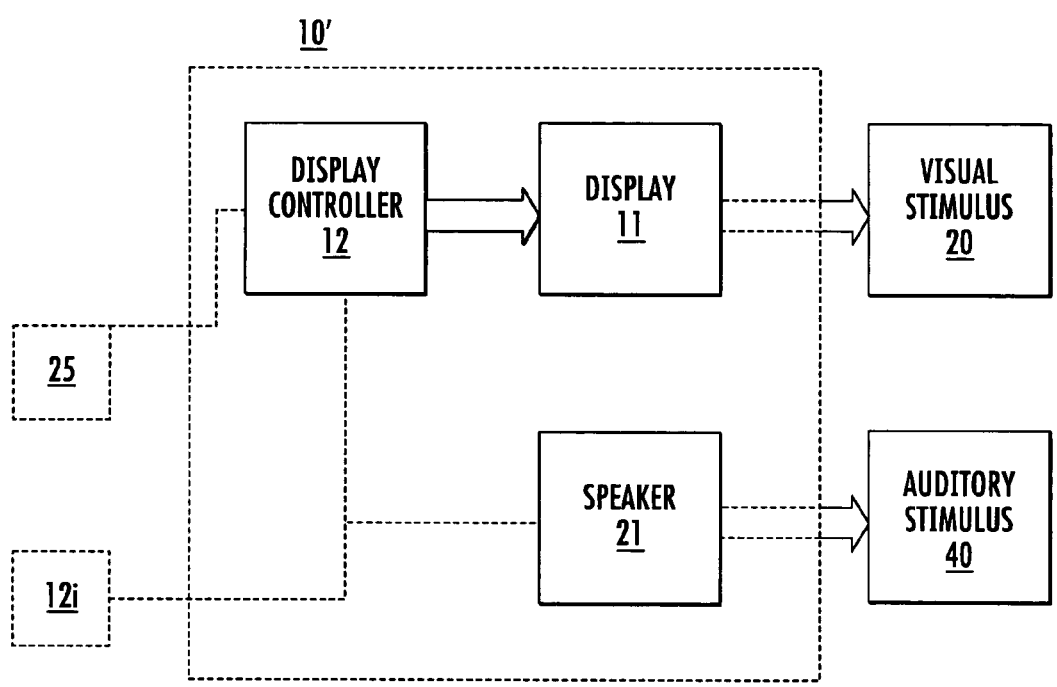
FIG. 5 is a schematic illustration of an additional device according to embodiments of the present invention.

As noted above, and as shown schematically in FIG. 5, the device 10' can be configured to provide both a visual speech gesture stimulus 20 and an auditory stimulus 40, such as an auditory speech gesture signal, which is preferably incongruent with (unrelated to) the visual speech gesture stimulus. For example, the device 10' can display the visual stimulus 20 as described above, and also output a selected auditory stimulus from a speaker 21. The patient may view the visual stimulus 20 to facilitate fluency, but begin to experience a period of non-fluency, whereupon the auditory stimulus 40 can be activated to relay an auditory stimulus comprising a sustained spoken vowel, consonant, vowel train, or the like, to the user to further facilitate fluency. Thus, the auditory stimulus 40 is independent and incongruent with the visual stimulus 20 (it is not merely an attendant auditory component of the speech of the visual display). The device 10' is preferably configured to store and transmit at desired times, the auditory stimulus 40, to the user or patient, such as relayed proximate in time to, or, preferably, substantially contemporaneously with a speaking event (while the patient or user is speaking).

The auditory stimulus 40 can be provided by a speaker 21 (FIG. 5) which, for example, may be incorporated into the body of the handheld display device 10 or can be provided via a peripheral component such as portable miniaturized devices such as ITE (in the ear), BTE (behind the ear) or OTE (over the ear) stuttering aid devices (not shown). The ear configured auditory stimulus 40 output devices can be configured as either a monaural or binaural input devices to the user (residing in or proximate to a single or both ears).

Alternatively, the auditory speech based stimulus 40 of the instant invention can be provided in a number of other ways. Recently, consumer electronics companies have proposed wearable devices (featuring a body area network) on a jacket. This device also includes a headset which can allow a user to listen to a phone call and music using the same headphone or headset and is configured to allow a user to switch between the two modes with a remote control switching device. This technology may be suitable to integrate the auditory stimulus speech signal of the present invention into a similar device so as to be output as an alternative to, or in addition to, the outputs now allowed so as to provide a multi-use output such as music, auditory stimulus speech signal, and listening to a phone call. Thus, the auditory stimulus 40 signal can be output from the headset upon activation of the output via a remote control unit in order to relay and output the second speech signal into the headset while the user is listening to a phone call via the same headset. See e.g., *New Wired Clothing Comes With Personal Network*, cnn.com/2000/TECH/computing/8/18/wiredjacket.idg/index.html (posted on Aug. 18, 2000). The content of this document is hereby incorporated by reference as if recited in full herein.

Preferably, the visual stimulus 20 and the auditory stimulus 40 are "exogenously" created which means generated by a cause external of the user, preferably by a person other than the patient/user, or, if generated by the user, that the stimulus signal is pre-recorded at a time in advance of use. It will be appreciated that neither the visual stimulus 20 nor the auditory stimulus 40 requires in situ manipulation or feedback of the user's contemporaneous speech and each is incongruous with the content of the user's speech.

Th exogenous auditory stimulus 40 can be a natural or spoken speech signal (a voice gesture associated with a vocal cord) not contemporaneously generated by or associated with the contemporaneous speech of the speaker himself/herself nor associated with the visual speech gestures of the visual choral speech stimulus. The auditory stimulus 40 is also preferably configured not to interrupt (i.e., it doesn't delay or mask or otherwise manipulate) the actual contemporaneously uttered speech of the user. Thus, the auditory stimulus 40 speech signal is independent and unrelated to the contemporaneous speech of the user as well as unrelated to the visual choral speech stimulus and can be provided as an auditory stimulus concurrently with or as a supplemental tool or aid to the visual choral speech stimulus 20 to allow the user to speak at a substantially normal pace with enhanced fluency.

The auditory speech stimulus 40 is preferably a natural spoken speech signal which can be coherent or incoherent (i.e., the exogenously generated auditory natural speech signal can have comprehensible meaning to the user or it can have no meaning to the user, rather, the natural speech signal can be a voice gesture or a collection of voice gestures). The auditory speech signal stimulus may be provided to the patient/user such that it is in the same language as that of the primary language of the user. Alternatively, the auditory speech signal may be generated by speech spoken in a language which is different from the primary language of the user.

The exogenously generated auditory-based speech signal can be either stuttered or fluent. The auditory-based speech signal can comprise a prolonged voice gesture or vocal spoken sound such as a prolonged single vowel or consonant or a combination of vowels and/or consonants, either alone, or in combination, as will be discussed further below. Further, the auditory stimulus speech signal of the instant invention can be provided to the patient in an intermittent manner (such as with a 25–75% duty cycle, or combinations thereof) while the patient or user is speaking (i.e., such that it is intermittent during speech production on the part of the patient/user). Alternatively, the auditory stimulus signal can be provided such that the signal is sustained for a period of time, or such that the auditory stimulus is substantially continuously transmitted to the user during speech production.

It is preferred that the exogenously generated auditory speech signal is generated by someone other than the user. The auditory stimulus speech signal may be able to be generated by a device, such as an elongated tube, which is configured so as to substantially replicate a voice or vocal tract or cord associated with the voice gesture sound of a person, so that, in operation, the replicated voiced speech signal can trigger the auditory cortex of the stutterer/user.

The exogenously generated auditory speech signal can be generated to include a prolonged spoken voice gesture (emphasizing a selected spoken sound). For example, the auditory speech signal may include at least one spoken prolonged syllabic sound (such as the last sound in the word "sudden") or a sonorant or continuant sound. As used herein the term "prolonged" means to emphasize or sustain the voice gesture sound over normal speech patterns, and preferably means to sustain the voice gesture in substantially steady state form for about at least 2–30 seconds. The auditory speech stimulus signal may also include a spoken simple sustained or steady state vowel in whatever appropriate language (whether a Romance language or other human spoken language). For example, in the English language, a simple sustained /a/, /i/, /e/, /o/, /u/, and /y/.

The exogenously voiced speech signal may include trains of vowels such as a three-vowel train. For example, in the English language, a three vowel train representing the three corner of the vowel triangle /a-i-u/ or other vowel trains or serially uttered sustained vowel sounds. Similarly, the auditory stimulus can include consonant trains or serially uttered (preferably prolonged or sustained) consonant and/or vowels or combinations thereof or sonorant or continuant sounds.

The auditory stimulus may be delivered to the user or stutterer such that it has a sustained duration of at least between about 5 seconds-2 minutes. More preferably, the auditory stimulus is transmitted such that it has a duration which is at least about 5–10 seconds and provided, as needed or desired, every 10–30 seconds to every 1–2 minutes (which can be repeated at the same time intervals or can be intermittently transmitted closer and further apart in time) during ongoing speech production by the patient such that the auditory stimulus signal is relayed to the user intermittently throughout the speech production on the part of the user. It should also be noted that the auditory speech stimulus signal can be recorded as a single short signal (such as about a 1–5 auditory stimulus signal) which can then be looped to provide a longer length output second speech signal. For example, an exogenously generated speech signal having a 1 second (in duration) length can be electronically (such as by digital or analog means) looped 10 times to output a 10 second signal to the user. The device 10 can also have a selectable duty cycle or timing function input to allow a user to select or vary the desired duration or output transmission cycle (not shown). Further description of some suitable auditory stimuli 40 are described in co-pending and co-assigned U.S. patent application entitled, *Methods and Devices for Delivering Exogenously Generated Speech Signals to Enhance Fluency in Persons Who Stutter*, identified by Attorney Docket No. 5218-83.

Turning again to the visual stimulus 20, the visual choral speech gestures of the instant invention may be stored as a digital or analog representation of the visual speech gestures to be output on the display for viewing by the patient/speaker. For example, the visual speech gestures can be electronically stored in digital format on a storage medium and subsequently displayed to the patient/speaker at desired times as needed by the patient during speech production. As such, the visual choral speech gestures may be recorded and stored in advance of use such that it can be conveniently and reliably visually displayed to the speaker/patient at a desirable time (and repeatable at appropriate times) such as when a person starts to stutter or is experiencing a stuttering event, or even just at intervals during fluent speech to inhibit the onset of a stuttering event. The visual choral speech gestures may also be stored or pre-recorded on a storage medium such as on a standard visual displayable format including, but not limited to, a video tape such as VHS/Beta or 8MM, a CD ROM, a DVD, or other electronic or video storage medium. In this manner, the visual choral speech gestures can be repeatedly played back and/or visually transmitted to the patient at desired intervals or at appropriate times.

Whatever the storage media or format, in certain embodiments, the representation can be rendered such that the rendered representation can be selectively zoomed in and out by the patient so as to allow the patient to adjust the display to show the upper torso and head of a person (to display visual choral speech or visual speech gestures of the lips and mouth), or to focus or zoom in to the head or face or just lip, mouth, and/or jaw region of the digital representation of the movement of the person.

It is thought that the representation of the visual choral speech may alternatively be provided by simulations of articulatory movements of persons, such that the representation simulates, for example, in clay or animated form, the human anatomical figure (including the face and lips), or just a portion of the head or face such as the lower portion of the face or the portion of the face adjacent to the lips of a person.

As will be appreciated by one of skill in the art, the present invention may be embodied as a device, method, system, or computer program product. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be or include, for example, but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), video storage medium such as VHS/Beta or 8MM, a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, embedded processor or other programmable data processing apparatus to produce a machine, such that the instructions, which execute via the processor of the computer or other programmable data processing apparatus, create means to and implementing circuits configured to implement the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

Various embodiments of the operational aspects of the present invention will now be described with reference to FIGS. 3, and 6–7. Referring now to FIG. 3, a fluency enhancing visual display system according to embodiments of the present invention is illustrated. As is seen in FIG. 3, the system includes a display controller 10, such as a general-purpose microprocessor, a digital signal processor or a specific purpose processor which is operably associated with the display 11. The present invention should not be construed as limited to the particular configuration illustrated in FIG. 3 or 6–7 but is intended to encompass other configurations capable of carrying out the operations and/or functions described herein.

Figure 6:
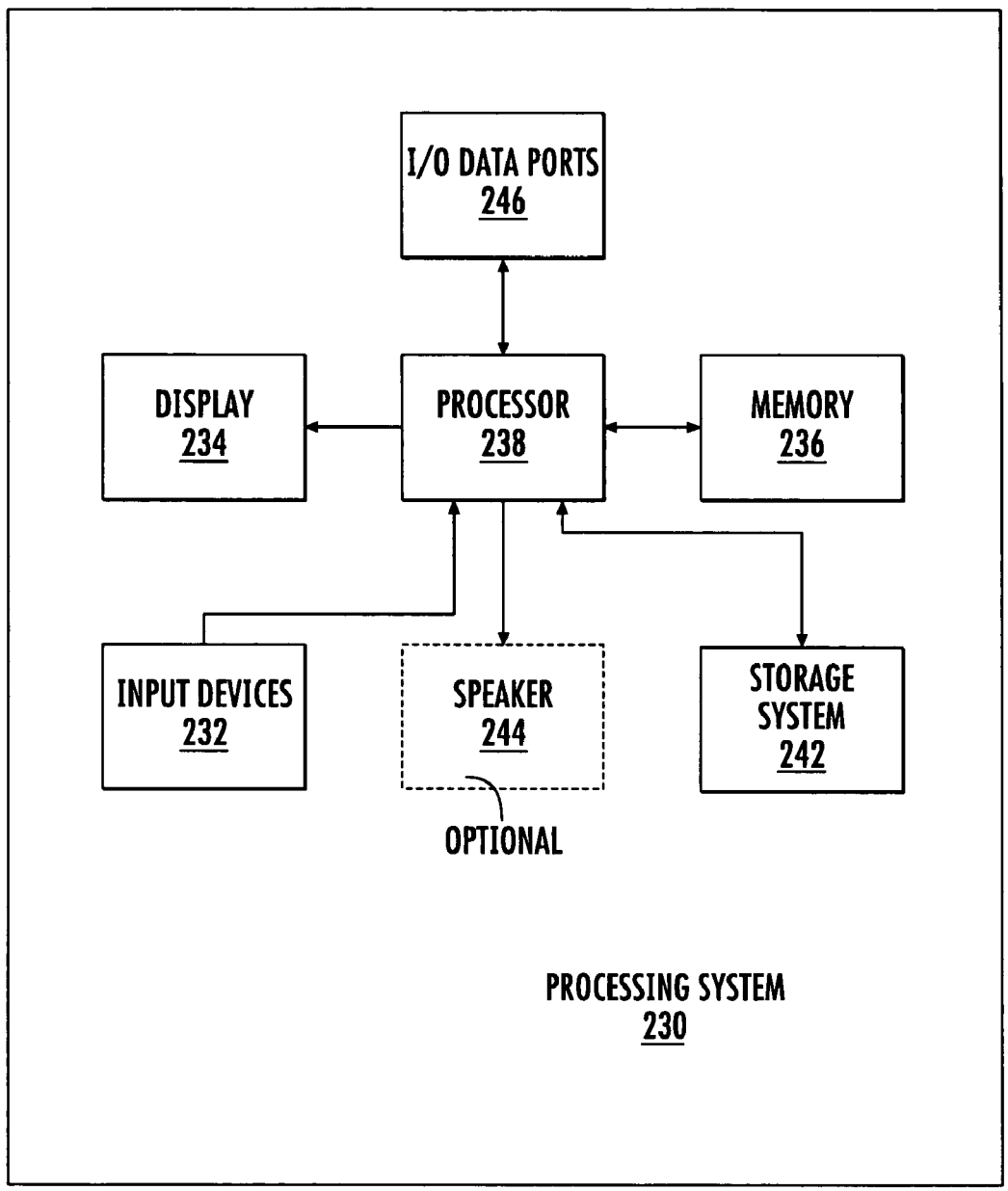
FIG. 6 is a schematic illustration of a processing system according to embodiments of the present invention.

An exemplary embodiment of a data processing system 230 suitable for use in accordance with embodiments of the present invention so as to provide the display controller 12 and the display 11 is illustrated in FIG. 6 and may include input device(s) 232 such as a keyboard or keypad, a display 234, and a memory 236, and a storage system 242 that communicate with a processor 238. The data processing system 230 may further include I/O data port(s) 246 or other such devices that also communicate with the processor 238. The I/O data port 246 can be used to transfer information between the data processing system 230 and another computer system or a network (e.g., the Internet) or to other devices controlled by the processor 238. These components may be conventional components such as those used in many conventional data processing systems which may be configured in accordance with the present invention to operate as described herein.

Figure 7:
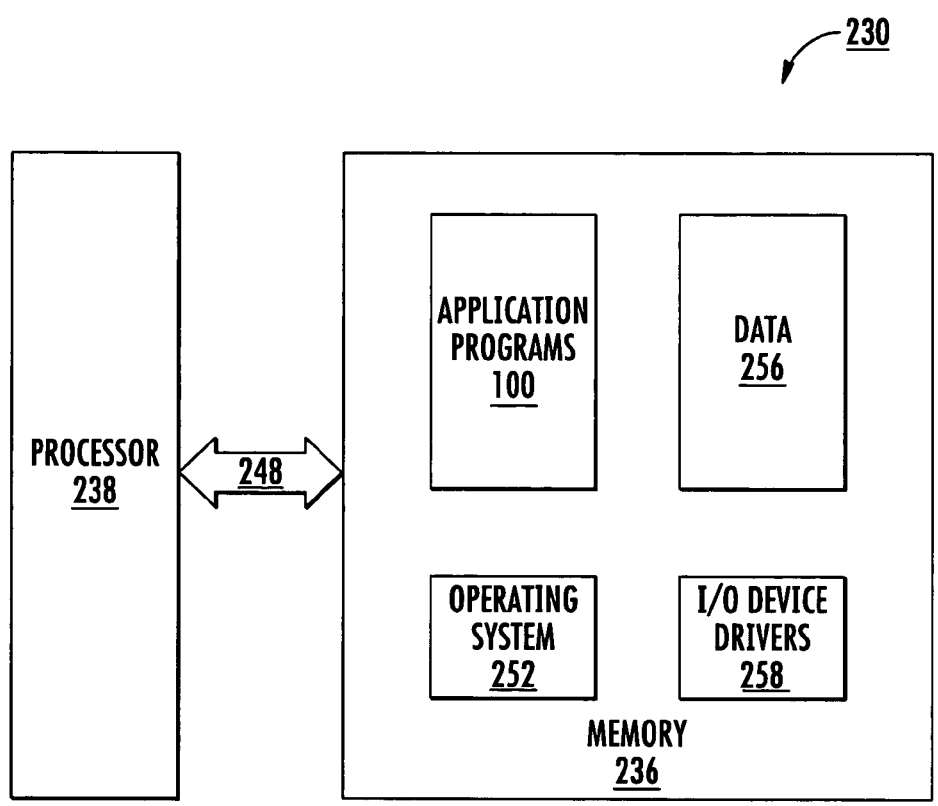
FIG. 7 is a schematic illustration of another processing system according to embodiments of the present invention.

FIG. 7 is a more detailed block diagram of data processing systems that illustrates systems, methods, and computer program products in accordance with embodiments of the present invention. The processor 238 communicates with the programmable memory 236 via one or more address/data bus(ses) 248. The processor 238 can be any commercially available or custom microprocessor.

The memory 236, is representative of the overall hierarchy of memory devices containing the software and data used to implement the functionality of the data processing system 230. The memory 236 can include both programmable and read-only memory. Typical memory devices may include, but are not limited to, static RAM (SRAM), dynamic RAM (DRAM), flash RAM, EEPROM, Read Only Memory (ROM), PROM, or other such memory devices. The read only memory may be of a type which may not be modified after its initial programming, such as ROM or PROM but may also be programmable in certain embodiments of the present invention.

Referring again to FIG. 7, the memory 236 may contain several categories of software and data used in the data processing system 230: the operating system 252; the input/output (I/O) device drivers 258; and data 256 which may include the visual stimulus image (and/or in the case of dual stimulus, the auditory stimulus as well). As will be appreciated by those of skill in the art, the operating system 252 may be any operating system suitable for use with a data processing system, such as OS/2, AIX or OS/390 from International Business Machines Corporation, Armonk, N.Y., WindowsCE, WindowsNT, Windows95, Windows98 or Windows2000 from Microsoft Corporation, Redmond, Wash., PalmOS from Palm, Inc., MacOS from Apple Computer, UNIX or Linux, proprietary operating systems or dedicated operating systems, for example, for embedded data processing systems.

The I/O device drivers 258 typically include software routines accessed through the operating system 252 to communicate with devices such as the input devices 232 (FIG. 6), the display 234 (FIG. 6), the I/O data port(s) 246 (FIG. 6), and certain components of the memory 236. The data 256 represents the static and dynamic data used by the operating system 252, I/O device drivers 258, and other software programs that may reside in the memory 236. The application programs 100 may include application programs for displaying the visual stimulus 20 and/or for providing the audio stimulus 40.

While the present invention is illustrated, for example, with reference to particular divisions of programs, functions and memories, the present invention should not be construed as limited to such logical divisions. Thus, the present invention should not be construed as limited to the configuration of FIG. 3 or 6–7 but is intended to encompass any configuration capable of carrying out the operations described herein.

The flowcharts and block diagrams of FIGS. 3 and 6–8 illustrate the architecture, functionality, and operation of possible implementations of processing systems for devices and systems according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

EXAMPLES

Experiments were conducted to determine if visual choral speech without the attendant auditory speech signal would induce fluency in persons whom stutter. Ten adults who stutter (eight males, two females, mean age 27.9 years, SD 9.4 years) participated. Participants did not present with any other speech, language, or hearing disorders and all had normal or corrected vision. Each participant had a history of therapy, and four were enrolled currently. While sitting across from a research assistant, participants viewed cue cards with printed text (three to seven words per card). The text for the cure cards was derived from numerous passages, taken from junior high school level textbooks, which have been used, in previous experiments. Participants were instructed to first read silently and then memorize the text on the cue card and repeat it in two different conditions. Participants were given one practice trial prior to data acquisition.

In the non-visual choral speech (NVCS) condition, participants recited the memorized portion aloud after the cue card was placed in their view. Following an initiation of signal, they were instructed to focus their gaze on the face, lips and jaw of the research assistant who sat motionless.

In the visual choral speech (VCS) condition, following the initiation signal, participants were instructed to focus their gaze on the articulatory movements of the face, lips and jaw of the research assistant who "silently mouthed the words" found on the cue card. If the participant stuttered a syllable, the experimenter would then repeat this same syllable until the end of the stuttering moment. Participants memorized and recited aloud at a normal rate of speaking 300 syllables in both conditions. Experimental conditions were counterbalanced between participants. Participants were instructed not to use any strategies or techniques to control or reduce defluencies.

Stuttering episodes were calculated from the first 300 syllables of participant's videotape recorded speech samples. Stuttering was defined as part-word repetitions, part-word prolongations, and inaudible postural fixations. The stuttering episodes were calculated by a trained research assistant. The same research assistant, for 10% of the speech samples chosen at random, recalculated stuttering frequency. Intrajudge syllable-by-syllable agreement was 0.80, as indexed by Cohen's kappa. Kappa values above 0.75 represent excellent agreement beyond chance. A second trained research assistant also independently determined stuttering frequency for 10% of the speech samples chosen at random. Interjudge syllable-by-syllable agreement, was 0.85 as indexed by Cohen's kappa.

The mean values for stuttering frequency for the NVCS and VCS conditions were 77.2 (SE=16.5) and 16.5 (SE=6.6) per 300 syllables, respectively. Stuttering frequency was reduced by approximately 80% in the VCS condition. A one factor repeated measures analysis of variance revealed that the reduction in stuttering frequency in the VCS condition was statistically significant [$F_{(1,9)}$=17.2, Greenhouse-Geiser P=0.0025, $\eta^2$=0.66]. For further details, see, Kalinowski et al., *Inducement of fluent speech in persons who stutter via visual choral speech*, 281 Neuroscience Letters, p. 1–3 (Elsevier Science Ireland Ltd, 2000).

The foregoing is illustrative of the present invention and is not to be construed as limiting thereof. Although described throughout as being particularly effective for persons who stutter, the present invention may also be effective to treat other speech impediments, impairments, and disorders.

Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for enhancing the fluency of persons who stutter, comprising steps of:
  displaying visual speech gestures associated with the articulatory movements of a person's mouth on a display while a patient having a stuttering or speech impediment is speaking so that the patient is able to visually perceive the articulatory movements of the person's mouth provided on the display such that the patient is able to refer to the display at desired times to thereby enhance the fluency of the speech of the patient.

2. A method according to claim 1, wherein said displaying step is carried out while the patient speaks at a substantially normal pace.

3. A method according to claim 2, wherein said displaying step is carried out substantially continuously during the speech of the patient.

4. A method according to claim 1, wherein said displaying step is carried out in advance of and temporally proximate to when the patient speaks.

5. A method according to claim 1, wherein said displaying step is performed such that any attendant auditory sound associated with the visual speech gestures of said displaying step is inaudible to the patient.

6. A method according to claim 1, wherein said displaying step is silent.

7. A method according to claim 1, wherein the visual speech gestures of said displaying step are generated by a person silently mouthing word passages of text with the displaying carried out substantially without attendant audible output of the words.

8. A method according to claim 1, wherein the linguistic content of the visual speech gestures is incongruous with the content of the speech output by the patient.

9. A method according to claim 1, wherein the visual speech gestures of said displaying step are performed at a substantially normal speech pace without displaying associated textual words and symbols.

10. A method according to claim 1, wherein the visual speech gestures of said displaying step correspond to articulatory movements of a person generating coherent speech, and wherein the displaying step is carried out without prominently displaying textual words and symbols associated with the coherent speech.

11. A method according to claim 1, wherein the visual speech gestures of said displaying step correspond to articulatory movements of a person generating incoherent speech.

12. A method according to claim 1, wherein said displaying step is directed directly into the retina of at least one eye of the patient.

13. A method according to claim 1, further comprising the steps of accepting user input to adjust the visual presentation of the displayed output of the visual speech gestures of said displaying step; and adjusting the visual presentation responsive to the user input.

14. A method according to claim 13, wherein the step of adjusting comprises zooming to enlarge the mouth region of the person making the visual gestures.

15. A method according to claim 13, wherein said displaying step is carried out in response to the onset of a stuttering event.

16. A method according to Claim 1, wherein said visual speech gestures of said displaying step are generated by at least one person.

17. A method according to claim 16, wherein the visual speech gestures are generated by a plurality of different persons speaking silently or with an inaudible speech output and generally concurrently.

18. A method according to claim 16, wherein the visual speech gestures are generated by a plurality of persons with different coherent speech output the persons being serially displayed to generate the visual speech gestures without audible attendant word sounds.

19. A method according to claim 18, wherein the visual speech gestures of the different persons of said displaying step are selectable by the patient during the displaying operation.

20. A method according to claim 1, wherein said visual speech gestures of said displaying step are simulated representations of at least a person's mouth and lips generating articulatory movements.

21. A method according to claim 1, wherein the display is carried on the frames of eyeglasses.

22. A method according to claim 1, wherein the display is operably associated with a telephone.

23. A method according to claim 22, wherein the telephone is wireless.

24. A method according to claim 1, wherein the visual speech gestures correspond to the articulatory movements of at least one person speaking textual matter recognizable to the patient in the language of the patient, and wherein the recognizable textual matter is incongruous with the speech content of the patient.

25. A method according to claim 24, wherein the visual speech gestures of the at least one person comprises articulatory movements of visual speech gestures associated with words corresponding to one or more of reciting nursery rhymes, poems, the lyrics of songs, speeches, national pledges, biblical passages, passages of books, and prayers, and wherein the displaying is carried out so that auditory output related to the words is generally inaudible to the user.

26. A method according to claim 25, wherein said visual speech gestures are displayed such that any auditory sound associated therewith is suppressed, wherein the visual speech gestures are incongruous with the speech of the patient, and wherein the visual speech gestures are generated based on normal paced fluent speech.

27. A method according to claim 1, wherein said displaying step is carried out such that the prominent image in the display is the person generating the visual speech gestures so that the articulatory movements are readily discernable by the patient.

28. A method according to claim 1, further comprising the step of generating an auditory stimulus configured to enhance speaking fluency of the patient which is audible to the patient, the auditory stimulus being unrelated to the visual speech gestures of said displaying step.

29. A method according to claim 28, wherein said generating step is separately selectable responsive to user input to initiate auditory output of the auditory stimulus which is audible to the patient based on said generating step.

30. A method according to claim 29, wherein the auditory stimulus is an independent and incongruent exogenously generated auditory spoken speech stimulus signal in the form of an entrained vowel or consonant.

31. A method according to claim 1, wherein said displaying step is carried out by the display which is integrated into one of a portable hand-held device, a general purpose computer, a wireless communication device, a watch, a head mounted display, and a telephone.

32. A method according to claim 1, wherein the displaying visual speech gestures associated with the articulatory movements of a person's mouth on a display is carried out to be devoid of text and word symbols in proximity to the mouth making the articulatory movements.

33. A device to enhance the fluency of persons who stutter, comprising:
a display device configured to display at least one visual speech gesture stimulus associated with the articulatory movements of a person reciting coherent language which is incongruous with the speech production of a user.

34. A device according to claim 33, wherein the device further comprises a display controller that is configured to repeatedly output the visual speech gesture stimulus to a user at desired times upon activation by the user corresponding to at least one of an episodic stuttering event on the part of the user, in advance of the production of speech by the user, and during the production of speech by the user.

35. A device according to claim 33, wherein said display device comprises a first operative standby mode and a second active display mode, and wherein said display device includes a user input circuit operably associated with the display device to cause the display device to enter the active display mode and display the visual speech gestures substantially immediate of a user activating said user input circuit.

36. A device according to claim 33, wherein said display device is configured to suppress attendant auditory sound associated with the visual speech gestures such that said visual speech gestures are displayed on said display device devoid of an audible attendant auditory output.

37. A device according to claim 33, wherein said visual speech gestures are substantially silently displayed on said display device to the user.

38. A device according to claim 33, wherein said device further comprises a speaker configured to output an auditory stimulus which is unrelated to the visual speech gesture stimulus, wherein the auditory stimulus is configured to be selectively activated by the user to be output separately or concurrently with the visual speech gesture stimulus.

39. A device according to claim 38, wherein the auditory stimulus is a natural spoken speech signal comprising a sustained speech sound, and wherein the natural spoken speech signal and the visual speech gestures are incongruous with the content of the user's speech.

40. A device according to claim 38, wherein said device is configured with a user activation circuit which allows the device to output in response to activation thereof, the auditory stimulus speech signal.

41. A device according to claim 33, wherein said device further comprises a user input zoom adjustment whereby the user can adjust the presentation of the visual speech gestures on the display in a manner which allows the user to readily discern the articulatory movements of the visual speech gesture stimulus while speaking at a substantially normal speech pace.

42. A device according to claim 33, wherein the device is configured to present on the display, in serialorder, a plurality of different persons providing a plurality of different visual speech gestures, each of the different visual speech gestures corresponding to coherent speech spoken at a substantially normal pace with the display device configured to display the visual speech gestures of the coherent speech without attendant audible output of words corresponding to the coherent speech.

43. A device according to claim 33, wherein said device is configured such that it is portable, and the display device is configured and sized to be removeably mountable to the head of the patient, and wherein, in use, the display device is sized and configured to reside proximate at least one eye of the user such that said visual speech gestures are visually relayed to the retina of the user.

44. A device according to claim 33, wherein the display device is incorporated into the body of a residence telephone or a wireless portable telephone.

45. A device according to claim 33, wherein the display device is incorporated into one of a portable device, a handheld device, a general purpose computer, a personal digital assistant, a wireless communication device, a watch, and a telephone.

46. A device according to claim 33, wherein said device is configured to be worn on the head such that the display device is positioned proximate one or both of the eyes and does not impede the entire field of vision of the user.

47. A device according to claim 33, wherein the display device is configured with a frame which is adapted to span across the face of the user and be supported by the nose and ears of the user such that the display device is configured as with two displays, each extending downwardly from the frame to overlie a portion of the eyes of the user.

48. A device according to claim 33, wherein said display device is configured to display the visual speech gesture stimulus such that the person making the articulatory movements is the prominent image in the display so that the articulatory movements are substantially continuously presented at the desired times in a manner in which the articulatory movements are readily discernable by the user during speech, wherein the display device is configured to provide the image of the articulatory movements without prominently displaying textual words and symbols associated with the coherent speech.

49. A device according to claim 48, wherein the visual speech gestures are presented on the display so that a mouth region of a person mouthing the coherent speech to provide the articulatory movements substantially fills the viewing area of the display.

50. A device according to claim 49, wherein the display device is configured to display the visual speech gesture stimulus so that any peripheral images surrounding the person generating the articulatory movements are arranged to inhibit distraction from the articulatory movements to reduce the likelihood of visual distraction from background images in the display.

51. A device according to claim 33, wherein the display is configured to generate the at least one visual speech gesture stimulus associated with the articulatory movements of a person reciting coherent language which is incongruous with the speech production of a user so that the display does not provide corresponding textual word or symbolic output.

52. A computer program product for enhancing the fluency of persons who stutter, the computer program product comprising:
 a computer readable storage medium having computer readable program code embodied in said medium, said computer-readable program code comprising:
 computer readable program code for displaying at least one visual speech gesture stimulus associated with the articulatory movements of a person's mouth on a display while a patient having a stuttering or speech impediment is speaking so that the patient is able to visually perceive the articulatory movements of the person's mouth provided on the display such that the patient is able to refer to the display at desired times, wherein the at least one visual speech gesture stimulus is provided by a person other than the patient.

53. A computer program product according to claim 52, wherein the at least one visual speech gesture stimulus is a plurality of different visual speech gesture stimuli, the different visual speech gestures stimuli corresponding to at least one of: (a) different persons generating the visual speech gestures associated with words of coherent speech; and (b) different articulatory movements on the part of a person providing the visual speech gestures associated with words of different coherent speech, and wherein said computer program product further comprises computer readable program code for visually displaying in serial order the different visual speech gesture stimuli.

54. A computer program product according to claim 53, wherein the visual speech gesture stimulus corresponds to coherent textual passages which are recognizable by the patient and incongruous wit the speech of the patient, and wherein said computer program product further comprises computer readable program code for accepting input from the patient to select the visual speech gesture stimuli to be displayed.

55. A computer program product according to claim 52, wherein the visual speech gesture stimuli corresponds to coherent language which is incongruous with the speech of the patient, and wherein the linguistic content of the visual speech gesture stimuli is recognizable by the patient and is output so that the visual speech gesture stimulus is substantially inaudible to the patient.

56. A computer program product according to claim 52, wherein the at least one visual speech gesture stimulus corresponds to a plurality of different visual speech gesture stimuli, and wherein said computer program product further comprises computer readable program code for code for serially displaying in a patient selectable format, the articulatory movements of at least one person speaking at least one of (a) the lyrics of a song (b) a poem, (c) a prayer (d) a passage from the Bible, (e) a passage from a story (f) a speech (g) and the Pledge of Allegiance to thereby enhance the fluency of a patient who stutters or has a speech impairment.

57. A computer program product according to claim 52, further comprising computer readable program code for accepting user input to adjust the visual presentation of the articulatory movements associated with the visual speech gestures.

58. A computer program product according to claim 57, wherein the computer program code for accepting user input to adjust the visual presentation includes computer program code accepting user input to zoom the image to enlarge the visual presentation of the articulatory movements displayed.

59. A computer program product according to claim 52, wherein the computer program code for displaying the visual speech gestures is configured so that the visual speech gestures of the articulatory movements of the person on the display is the prominent viewable image on the display and is associated with words of coherent speech such that the visual speech gestures are readily discernable to the patient while the patient is speaking and so that the visual speech gestures are substantially continuously displayed white the patient is speaking, the visual speech gestures being displayed generally without attendant audible verbal output.

60. A computer program product according to claim 52, further comprising computer program code for displaying the visual speech gesture images without (a) attendant audible speech sound, and (b) proximate textual or symbolic representation of the coherent speech.

61. A computer program product according to claim 52, further comprising computer program code for repeatedly displaying the visual speech gesture stimulus to the patient at desired times corresponding to one of an episodic stuttering event on the part of the patient, in advance of the production of speech on the part of the patient, and while the patient is speaking.

62. A computer program product according to claim 61, further comprising computer code for generating and providing an independent auditory stimulus that is configured to enhance speech fluency that is transmitted to the patient which is unrelated to the visual speech gesture stimulus.

63. A computer program product according to claim 62, further comprising computer program code for allowing the auditory stimulus to be selectively activated by the patient separately or concurrently with the display of the visual speech gesture stimulus.

64. A computer program product according to claim 63, wherein the auditory stimulus is a natural spoken speech signal which is incongruous with the speech of the patient.

65. A computer program product according to claim 52, wherein the computer readable program code for displaying the at least one visual speech gesture stimulus is configured to display articulatory movement of a mouth generating coherent words substantially without associated audible verbal utterances of the word and without textual word output or symbols of the coherent language proximate the mouth.

66. A portable device for enhancing fluency in stutterers, the device configured to display visual speech gestures of at least one person making articulatory movements by mouthing words associated with coherent speech, and wherein, in operation, the device is configured to provide the visual speech gestures with associated word utterances being generally inaudible to a user so that the user is able to visually perceive the articulatory movements of the person's mouth without attendant word sounds to thereby enhance the fluency of the speech of the patient.

67. A device according to claim 66, wherein the coherent speech is incongruent with the speech of the user and, wherein the coherent speech is associated with one or more of the person on the display reciting nursery rhymes, poems, the lyrics of songs, speeches, national pledges, biblical passages, passages of books, and prayers.

68. A device according to claim 66, wherein the coherent language is incongruous with the speech production of the user, and wherein the device does not display textual word or symbolic output associated with words of the coherent speech.

69. A device according to claim 66, wherein the device comprises a circuit configured to transmit an auditory stimulus that is that is configured to enhance fluency separately from the visual speech gesture stimulus and has auditory content that is unrelated to the visual speech gesture stimulus, the auditory stimulus being output so that it is audible to the user.

70. A device according to claim 66, further comprising user input configured to allow the user to selectively display the visual speech gesture at and/or for a desired time.

* * * * *